March 14, 1961 O. O. DUNHAM Plant Pat. 2,033
CHRYSANTHEMUM PLANT
Filed Oct. 28, 1959
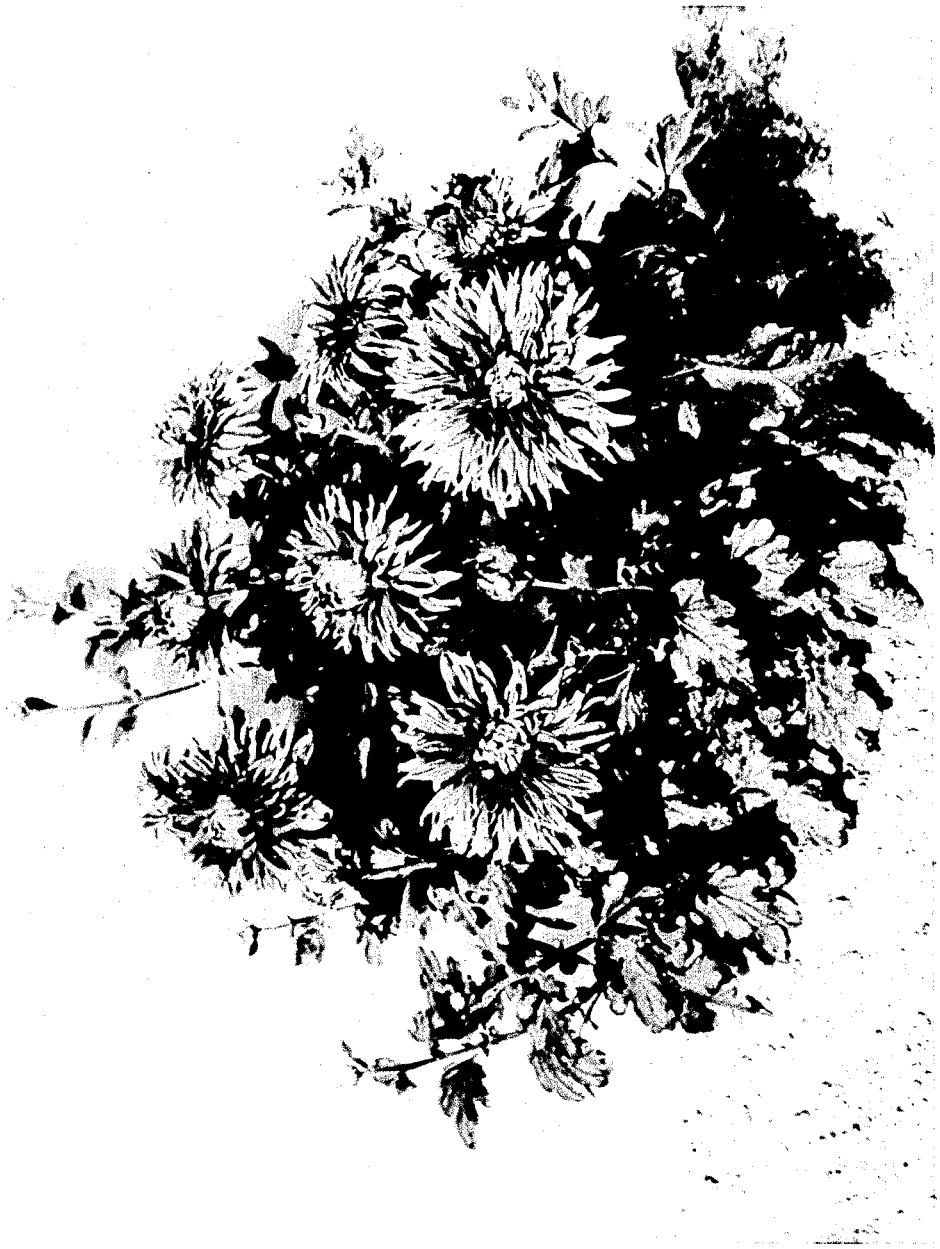
Inventor
O. O. DUNHAM
by Robb & Robb
attorneys United States Patent Office Plant Pat. 2,033
Patented Mar. 14, 1961

2,033

CHRYSANTHEMUM PLANT

Orville O. Dunham, Niles, Mich., assignor to George J. Ball Inc., West Chicago, Ill., a corporation Filed Oct. 28, 1959, Ser. No. 849,421

1 Claim. (Cl. 47—60)

My present invention comprises a new and distinct variety of chrysanthemum plant which is the result of crossing the variety "Show Girl" (unpatented), a variety of my own introduction, and the unpatented variety which I designate as No. 5350.

The object of my invention has been to produce a new variety of chrysanthemum plant of the *indicum* type, having a color somewhat like that of the parent "Show Girl" and embodies the early and continuous blooming characteristics of the parent No. 5350, with better plant habit and a quite different foliage from prior plants.

I have undertaken an extensive program of development in order to produce new varieties of chrysanthemum plants, and as a result of such program which has involved careful selection and cross-breeding, similar varieties have been produced of the type herein under consideration, which have characteristics of the broad parent classes, which include the American garden chrysanthemum and the English chrysanthemum. The desirable characteristics of the English early chrysanthemum have been produced in varieties derived therefrom and in the instant case, the earliness of the general type is again produced, with the continuous blooming characteristics of the American chrysanthemum being produced likewise.

The result of the specific hybridization previously mentioned, has been to produce my present new and distinct variety of chrysanthemum plant, which is characterized by the deep reddish purple to strong reddish purple color and very large size of its bloom, the very double arrangement of its petals, its better form and habit, the shiny green foliage with pointed lobes, and the early, continuous and long blooming period.

More specifically, the blooms of my new variety are of a deep reddish purple color (Nickerson Color Fan published by Munsell Color Company). As grown in the vicinity of Niles, Michigan, under uniform culture, plants of my new variety have grown to an average medium height of from 14 to 20".

My new variety bears a closer resemblance to the pollen parent "Show Girl" as to color but embodies the earliness and continuous blooming characteristics of the variety No. 5350, but in any event my new variety differs from both of its parents and other known varieties in many respects.

In comparing the color of the blooms of my new variety with the color of the blooms of the variety "Show Girl," it is found that the blooms of the latter are a much deeper purple whereas the blooms of my new variety are of a strong reddish purple (Munsell 2.57RP 3/8 to a strong reddish purple 2.5RP 5/10), the blooms of the parent "Show Girl" being of the Munsell hue 5P 3/9 to 5P 4/9.

The blooms of the instant variety are very large being of an average of 6 to 6½" (disbudded).

The petal arrangement in my new variety is very double and innumerable petals are found under normal conditions. As a result of the petal arrangement, the stamens are hidden as well as many petals likewise.

Under the conditions of culture previously referred to, which have taken place in the vicinity of Niles, Michigan, my new variety commences blooming early in September and continues until a killing frost, said blooming being both profuse and continuous until that time.

The buds of my new variety are very large and short with flat tops, the buds not being markedly affected by either hot or wet weather.

An important difference of the instant variety from either of its parents resides in the attractive shiny green foliage which is produced, said foliage having holly-like points on the lobes. This is both distinctive and different from either parent as pointed out and from other known varieties.

My new variety has been found to retain its distinctive characteristics through successive asexual reproduction.

My new variety has been asexually reproduced by cuttings in the vicinity of Niles, Michigan.

The accompanying drawing forming a part hereof shows a typical plant of my new variety of chrysanthemum plant.

The following is a detailed description of my new variety of chrysanthemum plant, the color references being to the Nickerson Color Fan published by Munsell Color Company:

Parentage: Seedling.
*Seed parent.*—No 5350 (unpatented).
*Pollen parent.*—"Show Girl" (unpatented).
Classification: Botanic—*Chrysanthemum indicum.*

*Flower*

Blooming habit: Blooms profusely and continuously from early to mid-September and until a killing frost. The observations were made in the vicinity of Niles, Michigan, in September.

Bud:
*Size.*—Very large.
*Form.*—Short with flat top. Not affected by hot or wet weather.
*Color.*—When petals begin to unfurl—2.5RP 5/10 washed with 2.5RP 6/10. When half blown: inside of petals—5RP 3/9 washed with 7.5RP 3/9; reverse of petals—7.5P 9/2.
*Sepals.*—Of no consequence.
*Calyx.* — Shape — funnel. Size — large. Aspect—hairy.
*Peduncle.*—Length—long. Aspect—rough. Color—medium green. Strength—stiff, erect, heavy. Opening—bud opens well and somewhat affected by adverse conditions.

Bloom:
*Size.*—Very large. Average size when fully expanded—6–6½" (disbudded).
*Borne.*—In clusters and irregular.
*Stems.*—Long, strong.
*Form.*—Flat. Permanence—retains its form to the end.
*Petalage.*—Very double. Number of petals under normal conditions innumerable.
*Color.*—Center of flower—2.5RP 3/8 washed with 2.5RP 5/10. Outer petals—2.5RP 4/10 washed with 2.5RP 6/10. Base of petals (singlet)—2.5RP 4/10. Inside of petals—2.5RP 4/10. Reverse of petals—2.5RP 9/2. General tonality from a distance—between 2.5RP 3/8 and 2.5RP 5/10.
*Discoloration.*—General tonality at end of: First week—retails same color. Second week—retains much the same color. Third week—retains much the same color.

Petals:
*Texture.*—Thin. Some fungus infection results in wet weather and some bleaching is caused by hot weather.

*Appearance.*—Inside—velvety. Outside—satiny.

*Form.*—Pointed.

*Arrangement.*—Imbricated.

*Persistence.*—Hang on and dry.

*Lastingness.*—On the plant—very long. As cut flower—very long.

Genital organs:

*Stamens, anthers.*—Small; few. Color—white.

*Arrangement.*—Regular around styles.

*Stamens, filaments.* — Medium. Color — lemon yellow.

*Pollen.*—Lemon yellow.

*Styles.*—Columnar.

*Stigmas.*—White.

*Ovaries.*—All enclosed in calyx.

*Plant*

Form: Bush.

Growth: Very vigorous, upright, branching, compact.

Foliage:

*Size.*—Very large.

*Quantity.*—Abundant.

*Color.*—New foliage—between 7.5GY 6/8 strong yellow green and 7.5GY 5/7 moderate yellow green. Old foliage—between 7.5GY 5/7 moderate yellow green and 7.5GY 4/4 moderate olive green.

*Shape.*—3 lobed.

*Texture.*—Upper side—glossy; smooth. Under side—velvety. Ribs and veins—ordinary.

*Edge.*—Holly-like points on lobes.

*Leaf stem.*—Color—green. Under side—smooth.

*Stipules.*—Short.

I claim:

A new and distinct variety of chrysanthemum plant substantially as herein described, characterized as to novelty by the deep reddish purple to strong reddish purple color and very large size of its blooms, the very double arrangement of its petals, its better form and habit, the shiny green foliage with pointed lobes, and the early, continuous and long blooming period.

No references cited.